(12) United States Patent
Erickson et al.

(10) Patent No.: US 10,035,555 B2
(45) Date of Patent: Jul. 31, 2018

(54) COGNITIVE STABILIZER WHEELS FOR VEHICLES

(71) Applicant: International Business Machines Corporation, Armonk, NY (US)

(72) Inventors: Thomas D. Erickson, Minneapolis, MN (US); Minkyong Kim, Scarsdale, NY (US); Clifford A. Pickover, Yorktown Heights, NY (US); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 98 days.

(21) Appl. No.: 15/203,320

(22) Filed: Jul. 6, 2016

(65) Prior Publication Data

US 2018/0009497 A1 Jan. 11, 2018

(51) Int. Cl.
| | |
|---|---|
| *B62J 27/00* | (2006.01) |
| *A61B 5/00* | (2006.01) |
| *A61B 5/11* | (2006.01) |
| *A61B 5/18* | (2006.01) |
| *H04W 4/02* | (2018.01) |
| *H04W 4/021* | (2018.01) |

(Continued)

(52) U.S. Cl.
CPC ............ *B62J 27/00* (2013.01); *A61B 5/0077* (2013.01); *A61B 5/1112* (2013.01); *A61B 5/1117* (2013.01); *A61B 5/18* (2013.01); *A61B 5/4803* (2013.01); *A61B 5/7275* (2013.01); *B62D 61/125* (2013.01); *B62H 1/12* (2013.01); *H04W 4/021* (2013.01); *H04W 4/027* (2013.01); *A61B 2562/0204* (2013.01); *B62D 61/12* (2013.01); *B62J 2300/0013* (2013.01)

(58) Field of Classification Search
None
See application file for complete search history.

(56) References Cited

U.S. PATENT DOCUMENTS

| | | | | |
|---|---|---|---|---|
| 4,691,798 A | * | 9/1987 | Engelbach | ............... B62H 1/12 180/209 |
| 5,064,213 A | | 11/1991 | Storch | |

(Continued)

FOREIGN PATENT DOCUMENTS

| | | |
|---|---|---|
| CN | 102722721 A | 10/2012 |
| CN | 103417219 A | 12/2013 |

(Continued)

OTHER PUBLICATIONS

Hirose, JP 2000190882 A (EPO machine translation Nov. 22, 2017).*

(Continued)

*Primary Examiner* — Kevin P Mahne
(74) *Attorney, Agent, or Firm* — Cahn & Samuels, LLP

(57) ABSTRACT

An embodiment of the invention provides a method and system including a sensor on a vehicle and a processor connected to the sensor. The processor determines a probability of falling based on input from the sensor, whether the probability of falling exceeds a threshold, and a state of an operator of the vehicle. An actuator connected to the processor receives a signal from the processor when the probability of falling exceeds the threshold and when the state of the operator includes an impaired state. Stabilizer wheels are connected to the actuator, where the signal includes a command to deploy the stabilizer wheels.

20 Claims, 3 Drawing Sheets

(51) Int. Cl.
    *B62D 61/12*     (2006.01)
    *B62H 1/12*     (2006.01)

(56) References Cited

U.S. PATENT DOCUMENTS

| | | | |
|---|---|---|---|
| 5,401,055 A * | 3/1995 | Pham | B62D 61/02 180/209 |
| 7,006,901 B2 * | 2/2006 | Wang | B60T 8/1706 180/218 |
| 7,141,026 B2 | 11/2006 | Aminian et al. | |
| 7,556,277 B2 | 7/2009 | Lytle | |
| 8,179,268 B2 | 5/2012 | Gannot et al. | |
| 2004/0098185 A1 * | 5/2004 | Wang | B60T 8/1706 701/70 |
| 2005/0167961 A1 * | 8/2005 | Murata | B62H 1/12 280/755 |
| 2007/0040341 A1 * | 2/2007 | Kaloust | B62D 1/283 280/5.509 |
| 2009/0254003 A1 | 10/2009 | Buckman | |
| 2013/0054126 A1 * | 2/2013 | Lazzari | B62D 37/06 701/124 |
| 2013/0082842 A1 | 4/2013 | Balazs et al. | |
| 2014/0180513 A1 * | 6/2014 | Kozloski | B60W 10/02 701/22 |
| 2015/0202939 A1 * | 7/2015 | Stettner | B60R 21/0134 701/37 |
| 2016/0280181 A1 * | 9/2016 | Poisner | B60R 25/00 |
| 2016/0339980 A1 * | 11/2016 | Koybayashi | B62J 37/00 |
| 2017/0120923 A1 * | 5/2017 | Rovik | B60W 30/18154 |

FOREIGN PATENT DOCUMENTS

| | | | |
|---|---|---|---|
| CN | 103731557 A | | 4/2014 |
| EP | 2575113 A1 | | 4/2013 |
| JP | 2000190882 A | * | 7/2000 ............ B62D 61/10 |
| WO | 2013054257 A1 | | 4/2013 |

OTHER PUBLICATIONS

Peters, Adele, "No More Training Wheels: This Bike for Kids Just Won't Fall Over", Fast Company, Jun. 27, 2014.
English Abstract of CN 103731557, Apr. 16, 2014.
English Abstract of CN 102722721, Oct. 10, 2012.
English Abstract of CN 103417219, Dec. 4, 2013.

* cited by examiner

COGNITIVE STABILIZER WHEELS FOR VEHICLES

BACKGROUND

The present invention relates to systems, methods, and computer program products for cognitive stabilizer wheels for vehicles. Children often use stabilizer wheels as they are learning to ride a bicycle (or before learning to ride a bicycle). Nevertheless, injuries can occur, including injuries to the head, groin, fractures (broken bones), soft tissue injuries, etc. Bicycles with stabilizer wheels are sometimes used by the elderly. Such bicycles can be used by those with a fear of falling, physical therapy patients, those with weight issues, cancer patients, those with cerebral palsy, stroke victims, adults or children who are physically impaired, and adults or children who are mentally handicapped.

SUMMARY OF THE INVENTION

An embodiment of the invention provides a method and system including a sensor on a vehicle and a processor connected to the sensor. The processor determines a probability of falling based on input from the sensor, whether the probability of falling exceeds a threshold, and a state of an operator of the vehicle. An actuator connected to the processor receives a signal from the processor when the probability of falling exceeds the threshold and when the state of the operator includes an impaired state. Stabilizer wheels are connected to the actuator, and the signal includes a command to deploy the stabilizer wheels.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Figure 1:
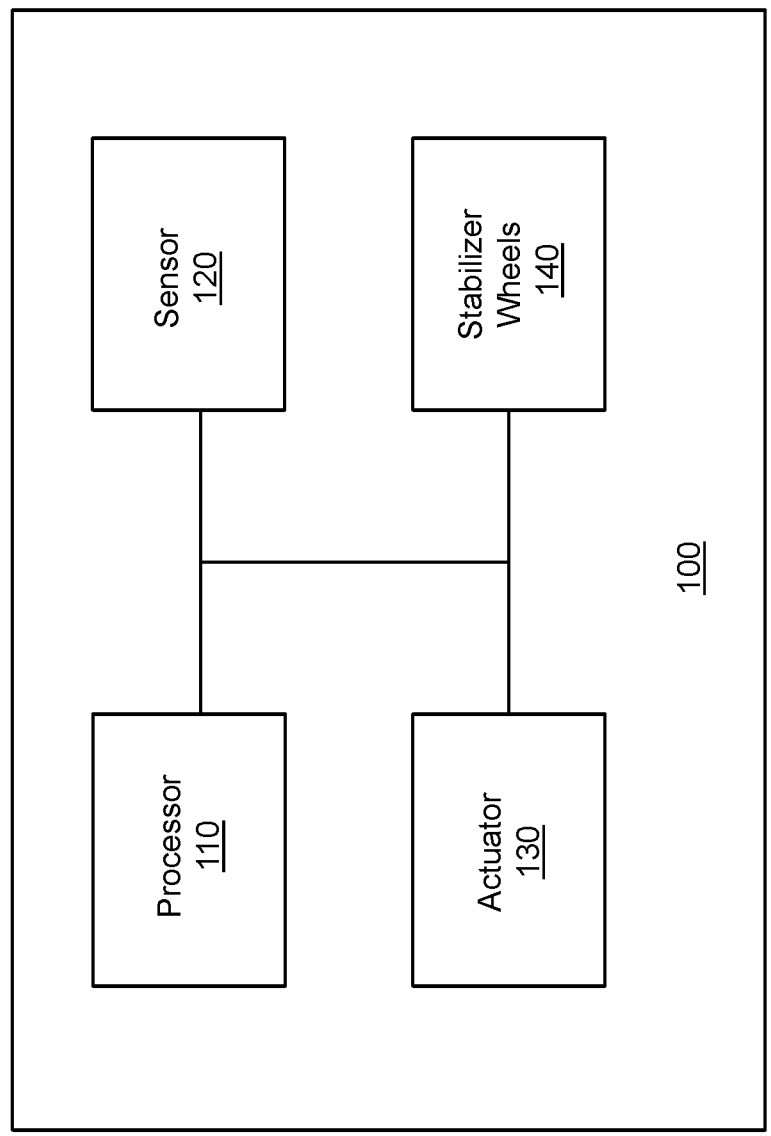
FIG. 1 is a diagram illustrating a system for cognitive stabilizer wheels for vehicles according to an embodiment of the invention.

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system that senses a bike rider who is falling, or is likely to fall, with a certain degree of confidence C (e.g., a child or elderly person), and determines a user's cognitive state. Based on the confidence level C and the user's cognitive state, a signal can be automatically sent to deployable stabilizer wheels. The cognitive state of the user (e.g., drowsy, intoxicated) may also be considered along with other conditions (e.g., Parkinson's disease). The system can help young people, the elderly, people with fear of falling, physical therapy patients, stroke victims, etc. As described below, machine learning techniques can be included for anticipating falls and other problems.

The signal sent to the stabilizer wheels may be conditioned based on a user profile, including cognitive and/or health state (e.g., pre-Alzheimer's, Parkinson's, autism, motor-control characteristics, etc.). Certain motor-control characteristics may be inferred by monitoring past falls or near-falls. As used herein, the term "near-falls" include instances where a user loses his or her balance on the vehicle, but does not fall off of the vehicle or the vehicle does not hit the ground (e.g., as detected by the sensor).

Similarly, the aforementioned characteristics and profiles may relate to any movement disorder that involves episodes or conditions such as an increased risk of controlling a bicycle or falling, such as but not limited to Wilson's disease, peripheral neuropathy, multiple sclerosis, chronic alcoholism, cerebellar damage, stroke, dementia, dementia with Lewy bodies, Alzheimer's disease, mercury intoxication, Hallevorden-Spatz disease, chorea, dystonias, ballismus, athetosis, dyskinesia, tic disorders, Tourette's syndrome, and fasciculation for example. Further, as used herein, the term "motor characteristic" may refer to a measurement, or monitoring of the movement of the a bicycle user during or before riding. Patients with movement disorders may at times have degraded or impaired motor characteristics. Although the exemplary embodiments herein describe use of the system in the context of bicycles, the system can also be utilized on vehicles other than bicycles, such as, for example, unicycles, scooters, skates, skateboards, wheelbarrows, and other devices with single or inline wheels.

Movement disorders are a broad category of disorders or syndromes that impact the health of a patient. At early stages of a disorder (or in cases where there is only a very minor impact on movement), a user still may be able to ride a bike safely, and bike riding may even have rehabilitate value, or emotional value, for someone recovering from an injury. In some areas of the world, a bike may be a very important means of transportation in the daily lives of people. Nonetheless, such movement disorders, which include Parkinson's disease, Wilson's disease and peripheral neuropathy, for example, are neurologic syndromes in which either the patient exhibits an excess of movement or a paucity of voluntary and automatic movements. Other types of disorders having movement impairment that may also be categorized as a movement disorder include multiple sclerosis, chronic alcoholism, cerebellar damage, strokes and dementia with Lewy bodies (Alzheimer's disease). These disorders are sometime marked by temporary conditions or episodes, such as a frozen gait for example, which may require an intervention to alleviate or facilitate an end to the condition.

The road surface may be taken into account, when it can be known or estimated. For example, through the use of a video camera or a monitoring of a bike's response to a road surface, road hardness and other characteristics may be estimated. In at least one embodiment, the bicycle includes a sensor and a processor, where the sensor identifies a pothole or other road obstruction, and the processor lifts up the stabilizer wheels to prevent the bike from getting stuck in the pothole or road obstruction. Once the bikes passes the obstruction, the processor can quickly activate the stabilizer wheels to prevent a fall. The processor can determine if the risk of falling is greater or lesser if the wheels are deployed, based on the forecast of a pothole encounter.

The stabilizer wheels may be deployed or retracted only within an area of high risk and/or at certain speeds. To prevent a stabilizer wheel from hindering a turn, the system (e.g., the processor sensors in the handle bar) can analyze the pressure/tension graphs of the wheels to differentiate falling from turning. When the system identifies that the bicycle is turning and not falling, the system can adjust the stabilizer wheels (e.g., by lifting or removing the pressure of the wheel joints) to prevent the stabilizer wheels from hindering the turning action. When the system identifies that the bicycle is falling, the system can adjust the stabilizer wheels (e.g., by adding pressure/making the joint rigid) to prevent falling.

The deployment/retraction of stabilizer wheels may be performed only within an area of a history of falls. The deployment/retraction of stabilizer wheels may be performed only within a specific radius (or specific surrounding area) of the current location of one or more high risk persons as identified by their cognitive state (e.g., nauseous, drowsy).

The cognitive stabilizer wheel deployment/retraction may be performed based on a forecast (and learning) of a potential fall and/or a likely location of a potential fall. Information regarding where bikers have fallen can be shared with other bikers. The information can be sent to the server side, and the server can share this information with other bikers based on their current location collected through location tracking devices such as GPS. The client side can be implemented as an application for easy access from mobile devices.

A confidence level C of an impending fall may be estimated in real-time, and if the level of C is above a threshold value, the cognitive stabilizer wheel deployment/retraction can be triggered. The threshold may be set by the user, a caregiver, and/or it may be learned and involve machine learning.

The sensing of a bike rider falling may be based on an accelerometer, video, a Passive Infrared (PIR) detection unit having a given field of view, a machine vision/depth camera, a smartphone-based real-time falling detection system, and/or a wearable human body falling detection device that can include embedded type multi-sensor hardware and falling detection software, etc. Sensing a bike rider falling may be based on fusing the output of multiple machine learning models trained on different modalities. In at least one embodiment, the system includes a remote control held by an adult supervisor, who can remotely deploy the balancing mechanisms when the adult observes that the child may be losing his or her balance.

The system may employ a stabilizing device for a bicycle that includes two hinged portions on each side of the rear wheel axles, one hinged portion being attached to the bicycle frame, and the other hinged portion supporting a stabilizer wheel. A compression spring can acts between each pair of associated hinged portions to increase the restoring forces on the bicycle when the bicycle tilts to one side on a turn, while the spring on the other side maintains the stabilizer wheel in contact with the ground. The spring tension and the amount of deployment (e.g., touching the road or 1 inch above the road) may be controlled by the cognitive state information, along with information on history of falls, cohorts, fall forecasting, etc.

Fall detection may also involve monitoring of human body posture change by embedded multi-sensor hardware through an acceleration sensor and a tilt angle sensor. Fall detection software may be used for judging whether the abnormal behavior of falling occurs. When falling occurs, a notice may be given to a far end for medical assistance through the General Packet Radio Service (GPRS) and the Global Position System (GPS). A measured human body posture signal may be filtered by the falling detection software and multiple characteristic quantities may be extracted. Training of multiple support vector machine (SVM) parameters and the weighting coefficient of each SVM may be performed to form an SVM integrated classifier. Data acquired in real time can be input into the falling detection software for detection. According to one or more wearable human body falling detection devices, a classifier can be used for providing help when an emergency occurs.

A person at risk can be identified based on his or her cognitive state, which may include nauseous, drowsy, intoxicated, fatigued, and/or stressed. The software controlling the cognitive stabilizer wheels can function as a personal productivity application because the cognitive stabilizer wheels may allow the infirm or physically challenged increased productivity, mobility, and independent living because the consequences of falling can be mitigated. If the cognitive stabilizer wheel system does detect an actual fall, appropriate signals and alarms may be transmitted to trained personnel.

The system may further anticipate the user's behavior and trajectory/path, and it may detect intention to change or cross a lane (e.g., lanes for pedestrians, walkers, runners, bikes, cars), further increasing the potential of fall/instability. Based on changes in this potential, the cognitive stabilizer wheels may be deployed, and the spring tension and the amount of deployment may be changed.

The system may observe the location and proximity of other cyclists and the likelihood of collision, which also may also trigger extension of the stabilizer wheels. Communication between controllers for cognitive stabilizer wheels may be used to control a "collaborative crashing of bicycles" when crashing is inevitable, to minimize the overall risk of injury (e.g., due to falling). As an example, if bicycle A is about to crash with bicycle B, the stabilizer wheel characteristics may change in a collaborative fashion.

The stabilizer wheels can include built-in sensors that detect how much weight is being put on them (i.e., the degree to which they are acting to prevent a fall). This can allow the system to track "virtual falls" and "near falls", and provide more data for the system to learn to anticipate its user's difficulties. The system can also include audio feedback to support the creation of training systems with a game-like character, where sound effects can signal that a virtual fall has happened or that a user has successfully avoided a fall.

In at least one embodiment of the invention, the stabilizer wheels include actuators that control the extension, stiffness and other properties of the stabilizer wheels that affect their ability to provide stabilization. This can increase the efficacy of the stabilizer wheels in providing stabilizing support. In particular, this could allow the system to adapt so as to provide the minimum amount of support needed, a property that may be useful in allowing a user to improve their ability to balance.

In a specific embodiment, a set of actuator-enhanced stabilizer wheels is programmed to reproduce the bumps and other perturbations of a mountain-biking trail, so that users could train for a race or other event taking place in a remote location. The system could also be used to allow another person in a training or oversight role (e.g., a parent, an occupational therapist) to replay the trainee's ride to experience a simulation of the unsteadiness experienced by the trainee.

When a fall or near fall occurs, a controller can communicate its data about the user and the circumstance and the incident to a central server, where machine learning techniques can be used to better improve the algorithms for anticipating falls and other problems. Improved algorithms can be broadcast to multiple sets of stabilizer wheels.

Figure 2:
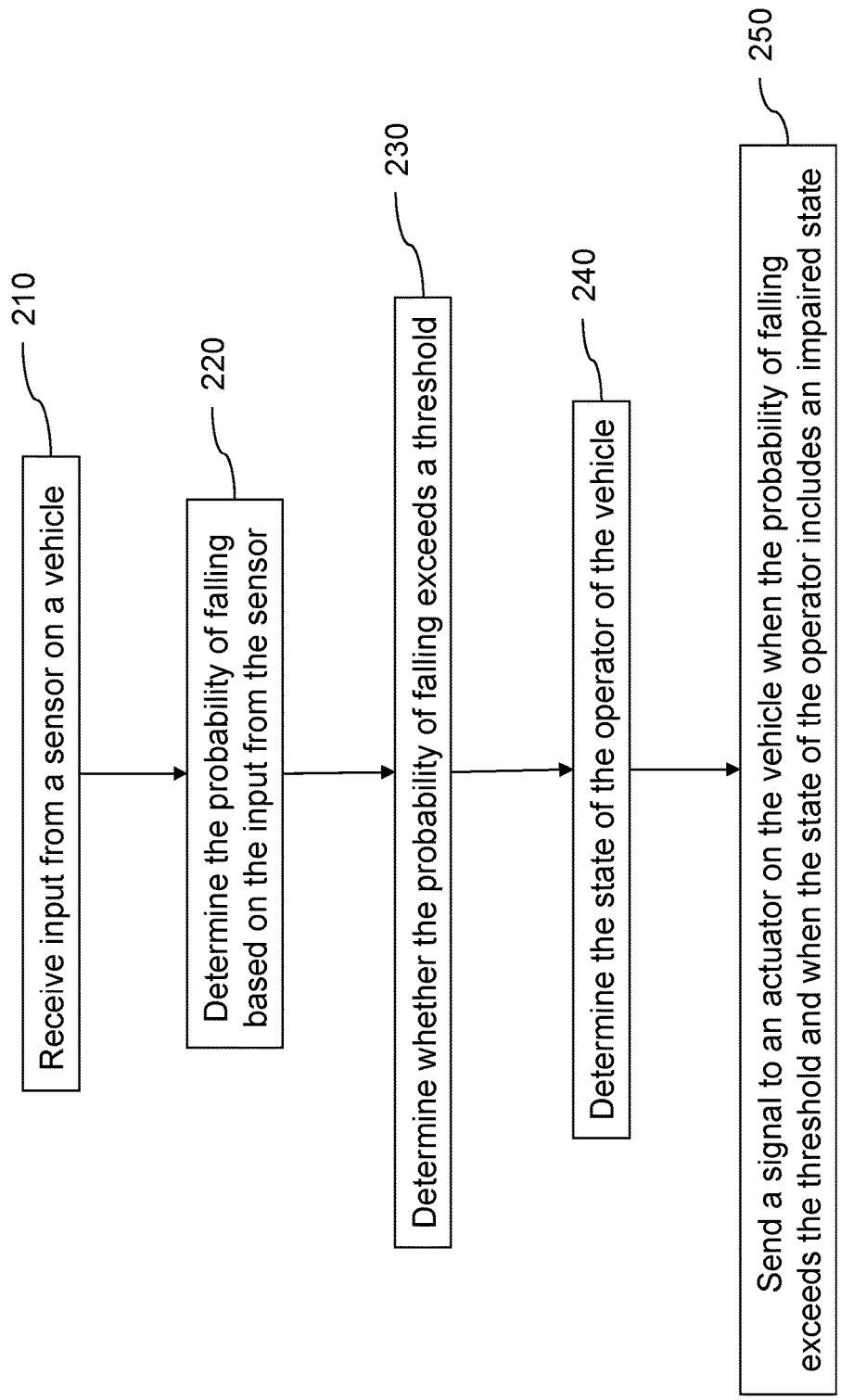
FIG. 2 is a flow diagram illustrating a method for using cognitive stabilizer wheels for vehicles according to an embodiment of the invention.

FIG. 1 is a diagram illustrating a system 100 for stabilizer wheels for bicycles according to an embodiment of the invention. FIG. 2 is a flow diagram illustrating a method for using stabilizer wheels for bicycles according to an embodiment of the invention (e.g., using the system 100). A processor 110 can receive input from a sensor 120 (examples) on a vehicle (210). As described above, the sensor can include an accelerometer, a camera, a PIR detection unit, a smartphone, a wearable human body falling detection device which is composed of embedded type multi-sensor hardware and falling detection software, or any combination thereof. As used herein, the term "vehicle" includes motorized and human-powered devices for transporting humans, such as, for example, a unicycle, a bicycle, a scooter, and a motorcycle.

The processor 110 can determine the probability of falling based on the input from the sensor 120 (220). As used herein, the term "processor" includes a computer hardware device, such as, for example, a central processing unit (CPU), an integrated circuit, or a microprocessor. The processor 110 can also determine whether the probability of falling exceeds a threshold (230). The threshold can be set and/or modified by the manufacturer of the system, the operator of the vehicle (also referred to herein as a "user"), or a supervisor, such as a parent, teacher, physical therapist, or doctor. As described below, the threshold can be modified by the processor 110 based on the operator's riding and falling history.

In addition, the processor 110 can determine the state of the operator of the vehicle (240). For example, the processor 110 can determine the cognitive or emotional state of the operator by analyzing a facial expression of the operator captured by a camera (e.g., on the handlebars of the vehicle). In another example, the processor 110 can determine the cognitive or emotional state of the operator by analyzing audible input captured by a microphone (e.g., on the handlebars of the vehicle). The audible input can include detected keywords, tone of spoken words, frequency of the spoken words, and/or pitch of the spoken words.

The processor 110 can send a signal to an actuator 130 on the vehicle when the probability of falling exceeds the threshold and when the state of the operator includes an impaired state (250) (e.g., fatigued, nauseous, stressed, intoxicated, distracted, and drowsy), where the signal includes a command to deploy stabilizer wheels 140 on the vehicle. The processor 110 can estimate, with a certain confidence level, that a user (e.g., bike rider) is distracted by, for example, detecting that the bike rider is talking while riding or looking to the side instead of forward as the bike travels forward using a helmet mounted camera and/or microphone. A profile of the operator can be created and maintained in an electronic database in or connected to the system 100. The profile of the operator can include a neurological disease state (e.g., Alzheimer's disease, pre-Alzheimer's disease, Parkinson's disease, Autism), a history of past falls, and/or a history of past near-falls. In a preferred embodiment, the signal may only be sent to the actuator 130 when the profile of the user includes a neurological disease, a number of past falls above a fall threshold, a number of past near-falls above a near-fall threshold, or any combination thereof.

In at least one embodiment, the system 100 identifies the riding surface condition with a camera on the vehicle (e.g., the processor 110 identifies that snow is present in an image captured by the camera) and/or an online resource (e.g., a weather website, map/website having riding surface conditions (e.g., gravel, dirt, sand, asphalt)). The signal may only be sent to the actuator 130 when the riding surface condition includes wet, snow, icy, slick, muddy, standing water, flooding, loose terrain, or any combination thereof.

In another embodiment, the system 100 identifies the location of the vehicle, for example, via a GPS device on the vehicle. The signal may only be sent to the actuator 130 when the location of the vehicle is within a predetermined area (e.g., can be set as within a radius from a select location). For example, the user, a system administrator, a parent, and/or a manufacturer identifies areas of high risk, such as high traffic, history of accidents, rough or uneven terrain, sharp curves, steep hills, etc. In addition, the system 100 can identify the speed of the vehicle, for example, via a speedometer on the vehicle. The signal may only be sent to the actuator 130 when the speed of the vehicle exceeds a speed threshold.

In another embodiment of the invention, the system 100 creates a log including readings from the sensor 120 and whether the vehicle fell at each reading. The log can be stored in an electronic database in or connected to the system. As used herein, the term "connected" includes operationally connected, logically connected, in communication with, physically or wirelessly connected, engaged, coupled, contacts, linked, affixed, and attached. The processor 110 can determine the probability of falling is based on the log. For example, when the log indicates that the user fell 82% of the time when at a 30 degree tilt, the processor 110 determines that the probability of falling is 82% when the sensor 120 indicates that the vehicle is at a 30 degree tilt. If the threshold is 80%, then the processor 110 will send the signal to deploy the stabilizer wheels to the actuator 130. When a fall or near fall occurs, data from the sensor 120 can be sent to a server where machine learning techniques can be used to better improve the algorithms for anticipating falls and other problems.

In at least one embodiment, the system 100 can identify the distance of an object (e.g., a tree, street sign, pedestrian, car, or other bicycle) to the vehicle with a sensor (e.g., the sensor 120). The signal may only be sent to the actuator 130 when the distance to the object is below a collision threshold (e.g., 1.5 feet). In another embodiment, the system 100 can identify a road obstruction, such as a pothole, in front of the vehicle with the sensor or the camera. The processor 110 can send a second signal to the actuator when the road obstruction is identified and the stabilizer wheels are in a deployed position. The second signal can include a command to retract the stabilizer wheels so that the stabilizer wheels do not get caught in the road obstruction.

The system 100 can also identify one or more high-risk areas based on the profile of the user, a riding surface condition, and/or location information. The location information can include information regarding where other operators have fallen in the past; and, the profile of the user can include information regarding where the user has fallen in the past. The signal may only be sent to the actuator 130 when the vehicle is in one of the high-risk areas.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
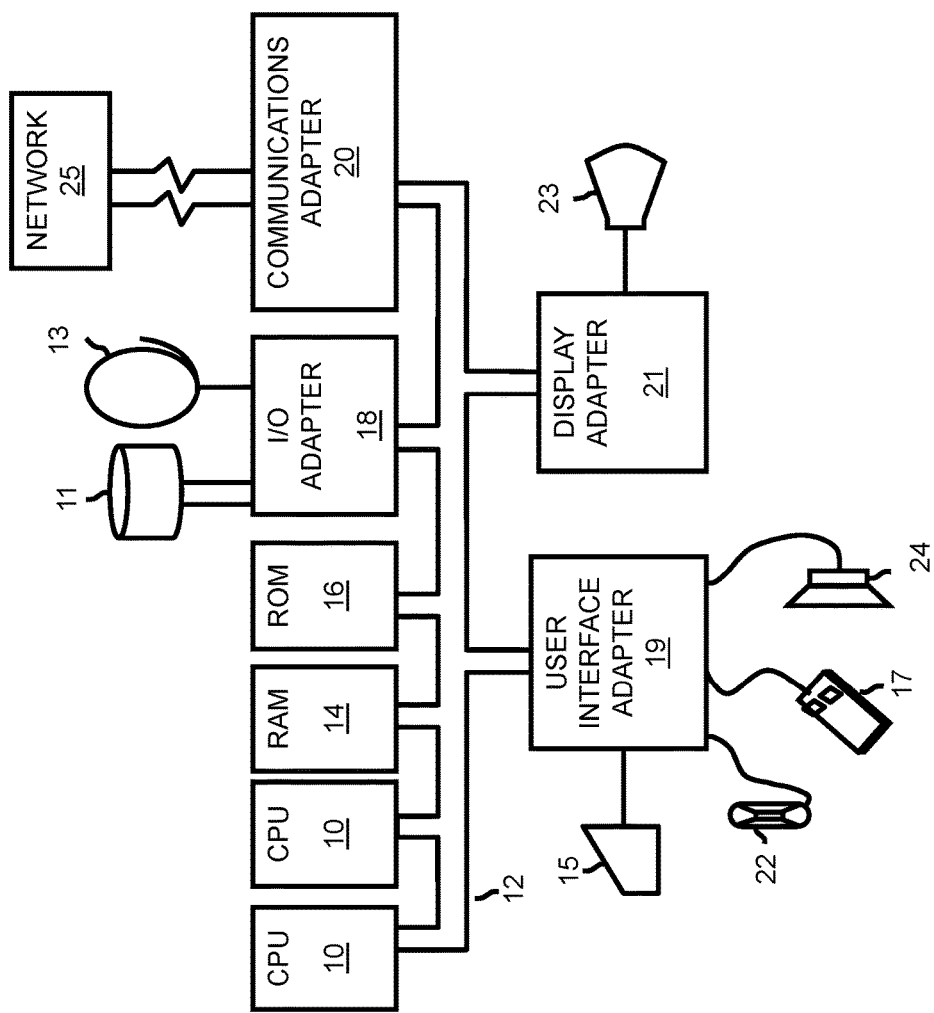
FIG. 3 is a diagram illustrating a computer program product for using cognitive stabilizer wheels for vehicles according to an embodiment of the invention.

Referring now to FIG. 3, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
receiving input from a first sensor on a vehicle;
determining a probability of falling based on the input;
determining whether an operator of the vehicle has an impaired state based on input from a second sensor; and
sending a signal to an actuator on the vehicle to deploy stabilizer wheels when:
the probability of falling exceeds a threshold;
the operator has an impaired state; and
an operator profile includes at least one of a neurological disease, a history of past falls, a history of past near-falls, or any combination thereof.

2. The method according to claim 1, wherein the impaired state is selected from the group consisting of fatigued, nauseous, stressed, intoxicated, distracted, and drowsy.

3. The method according to claim 1, wherein the input from the second sensor comprises a facial expression of the operator captured by a camera or audible input captured by a microphone.

4. The method according to claim 1, further comprising identifying a riding surface condition with an online resource.

5. The method according to claim 1, further comprising identifying a location of the vehicle via a GPS device on the vehicle, wherein the signal is sent to the actuator when the location of the vehicle is within a predetermined area.

6. The method according to claim 1, further comprising:
identifying a high-risk area based on at least one of the operator profile or location information where other operators have fallen in the past; and
sending the signal to the actuator when the vehicle is in the high-risk area.

7. The method according to claim 1, further comprising creating a log including readings from the sensor and whether the vehicle fell at each reading, wherein said determining of the probability of falling is based on the log.

8. The method according to claim 1, further comprising:
identifying a distance of an object to the vehicle; and
sending the signal to the actuator when the distance to the object is below a collision threshold.

9. The method according to claim 1, further comprising:
identifying a road obstruction in front of the vehicle; and
sending a second signal to the actuator when the road obstruction is identified and the stabilizer wheels are in a deployed position, the second signal including a command to retract the stabilizer wheels.

10. The method according to claim 1, wherein the threshold is set by a parent, teacher, physical therapist, or doctor.

11. The method according to claim 1, wherein the operator profile includes a history of past falls and a history of past near-falls.

12. The method according to claim 1, wherein the first sensor comprises an accelerometer, a Passive Infrared (PIR) detection unit, a smartphone-based real-time falling detection system, a wearable human body falling detection device, an acceleration sensor, or a tilt angle sensor.

13. A system comprising:
a first sensor on a vehicle;
a processor connected to said first sensor and a second sensor, said processor determines a probability of falling based on input from said first sensor and a state of an operator of the vehicle based on input from a second sensor;
an actuator connected to said processor
an electronic database connected to said processor and comprising an operator profile; and
stabilizer wheels connected to said actuator, wherein the signal includes a command to deploy said stabilizer wheels from said processor when:
the probability of falling exceeds a threshold;
the operator has an impaired state; and
the operator profile includes at least one of a neurological disease, a history of past falls, a history of past near-falls, or any combination thereof.

14. The system according to claim 13, further comprising a GPS device connected to said processor.

15. The system according to claim 13, wherein said electronic database includes readings from said first sensor and whether the vehicle fell at each reading, wherein said processor modifies the threshold based on data in said electronic database.

16. The system according to claim 13, wherein the first sensor comprises a passive infrared detection unit.

17. The system according to claim 13, wherein the first sensor comprises an acceleration sensor or a tilt angle sensor.

18. The system according to claim 13, wherein the stabilizer wheels have built-in sensors that detect how much weight is put on them.

19. The system according to claim 13, further comprising sensors in a handle bar of the vehicle to differentiate falling from turning.

20. A computer program product comprising:
a computer readable storage medium having stored thereon:
first program instructions executable by a device to cause the device to receive input from a first sensor on a vehicle;
second program instructions executable by the device to cause the device to determine a probability of falling based on the input from the first sensor;
third program instructions executable by the device to cause the device to determine whether the probability of falling exceeds a threshold;
fourth program instructions executable by the device to cause the device to determine a state of an operator of the vehicle based on input from a second sensor;
fifth program instructions to maintain an electronic database comprising an operator profile; and
sixth program instructions executable by the device to cause the device to send a signal to an actuator on the vehicle to deploy stabilizer wheels when:
the probability of falling exceeds the threshold;
when the state of the operator includes an impaired state; and
the operator profile includes at least one of a neurological disease, a history of past falls, a history of past near-falls, or any combination thereof.

* * * * *